United States Patent
Bartsch et al.

(10) Patent No.: US 7,067,685 B2
(45) Date of Patent: Jun. 27, 2006

(54) PHOSPHONITES, USE THEREOF AS LIGAND IN TRANSITION METAL COMPLEXES AND METHOD FOR PRODUCTION OF NITRILES

(75) Inventors: Michael Bartsch, Neustadt (DE); Robert Baumann, Mannheim (DE); Dagmar Pascale Kunsmann-Keitel, Limburgerhof (DE); Gerd Haderlein, Darmstadt (DE); Tim Jungkamp, Dossenheim (DE); Marco Altmayer, Mannheim (DE); Wolfgang Siegel, Limburgerhof (DE); Ferenc Molnar, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 37 days.

(21) Appl. No.: 10/491,918

(22) PCT Filed: Oct. 4, 2002

(86) PCT No.: PCT/EP02/11107

§ 371 (c)(1),
(2), (4) Date: Apr. 8, 2004

(87) PCT Pub. No.: WO03/033509

PCT Pub. Date: Apr. 24, 2003

(65) Prior Publication Data

US 2005/0090678 A1    Apr. 28, 2005

(30) Foreign Application Priority Data

Oct. 12, 2001  (DE) .................. 101 50 281
Feb. 20, 2002  (DE) .................. 102 07 165

(51) Int. Cl.
C07F 17/02  (2006.01)

(52) U.S. Cl. .............. 556/19; 558/156; 558/338; 502/213

(58) Field of Classification Search ............ 556/19; 558/156, 338; 502/213
See application file for complete search history.

(56) References Cited

U.S. PATENT DOCUMENTS 3,766,237 A  10/1973  Chia et al.
3,850,973 A  11/1974  Seidel et al.

(Continued)

FOREIGN PATENT DOCUMENTS

GB  1 377 228  12/1974

WO  99/64155  12/1999
WO  WO 99/64155  * 12/1999
WO  00/13983  3/2000

OTHER PUBLICATIONS

H. Schnidlbauer, Monatshefte Chemie, Band 96, 1965, Seite 1936-1942.

(Continued)

*Primary Examiner*—Johann Richter
*Assistant Examiner*—Chukwuma Nwaonicha
(74) *Attorney, Agent, or Firm*—Novak Druce & Quigg, LLP; Jason D. Voight

(57) ABSTRACT

The invention relates to phosphinites I of formulae (1) or (2), in which R1, R2, R5, R6, R7, R8, R9 independently represent hydrogen, an alkyl or alkylene group having 1 to 8 carbon atoms or an alkoxy group having 1 to 8 carbon atoms; R3 is H or methyl; R4 is i-propyl or t-butyl; X is F, Cl or $CF_3$ and n is 1 or 2

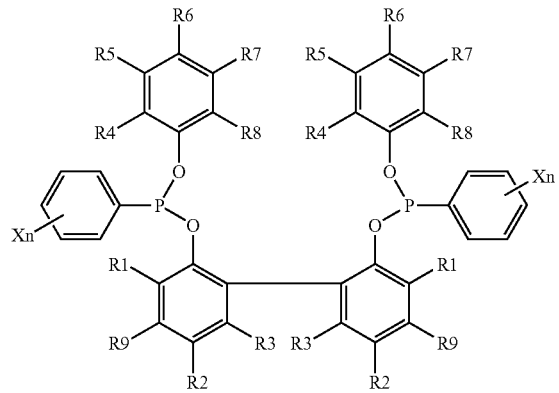

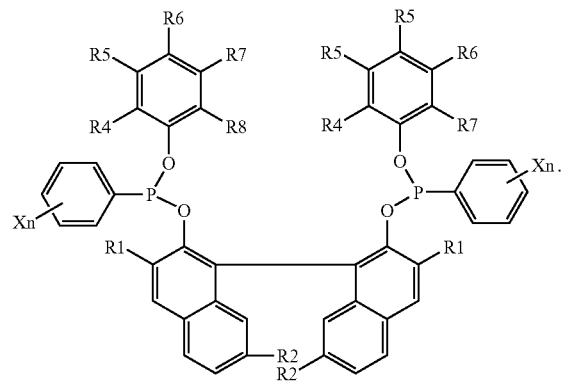

11 Claims, No Drawings

U.S. PATENT DOCUMENTS

| | | |
|---|---|---|
| 3,903,120 A | 9/1975 | Shook et al. |
| 4,493,906 A | 1/1985 | Couvillion |
| 4,587,369 A | 5/1986 | Cosyns et al. |
| 4,704,492 A | 11/1987 | Nemet-Mavrodin |
| 5,523,453 A | 6/1996 | Breikss |
| 5,693,843 A | 12/1997 | Breikss et al. |
| 5,981,772 A | 11/1999 | Foo et al. |
| 6,127,567 A | 10/2000 | Garner et al. |

OTHER PUBLICATIONS

Applied Homogeneous Catalysis with Organometalic Compounds, Bd. 1, VCH Weinheim, S. 479.

Ullmanns Enzyklopedie der technischem Chemie, Bd. 1, 3. Aufl., 1951, S. 743 ff.

Ullmanns Enzyklopedie der technischem Chemie, Bd. 1, 3. Aufl., 1951, S. 769 ff.

* cited by examiner

PHOSPHONITES, USE THEREOF AS LIGAND IN TRANSITION METAL COMPLEXES AND METHOD FOR PRODUCTION OF NITRILES

The present invention relates to novel phosphonites, in particular chelating phosphonites, methods of preparing them, their use as ligands in transition metal complexes, novel transition metal complexes, a process for preparing the complexes, their use as catalyst and processes carried out in the presence of such transition metal complexes as catalyst.

Chelating phosphonites, nickel complexes containing such phosphonites as ligands and the use of such complexes as catalysts are known.

WO 99/13983 and WO 99/64155 describe a process for the hydrocyanation of unsaturated organic compounds and the isomerization of nitriles in the presence of nickel(0) complexes containing chelating phosphonites as ligands. The chelating phosphonites described have good stability under the corresponding reaction conditions. It would be desirable to improve the stability of the chelating phosphonite ligands to increase the operating life of the catalyst. Furthermore, an improvement in the selectivity of the catalyst, for example to 3-pentenenitrile in the hydrocyanation of butadiene or to adiponitrile in the hydrocyanation of 3-pentenenitrile, and an improvement in the space-time yield are desirable.

It is an object of the present invention to provide phosphonites which are suitable as chelating phosphonites and display high, stability, high reactivity and high selectivity when used as catalysts in the hydrocyanation of unsaturated organic compounds and make it possible for such hydrocyanations to be carried out in a technically simple and economical manner.

We have found that this object is achieved by phosphonites I of the formula 1 or 2

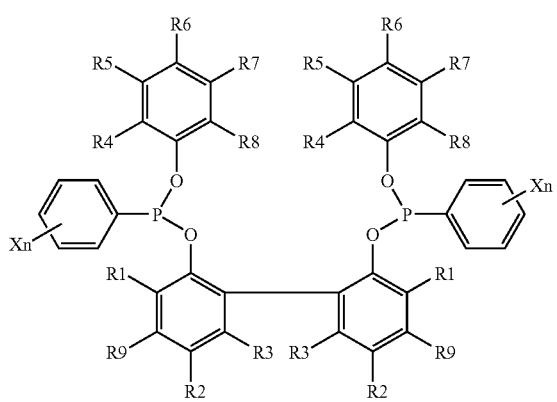

formula 1

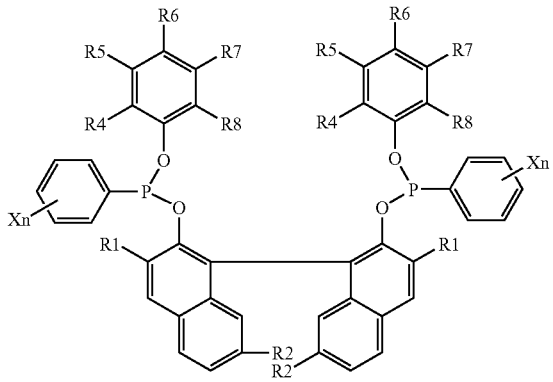

formula 2 where

R1, R2, R5, R6, R7, R8, R9 are each, independently of one another, hydrogen, an alkyl or alkylene group having from 1 to 8 carbon atoms or an alkoxy group having from 1 to 8 carbon atoms, R3 is H or methyl, R4 is i-propyl or t-butyl, X is F, Cl or $CF_3$ n is 1 or 2, and also methods of preparing them, their use as ligands in transition metal complexes, novel transition metal complexes, processes for preparing them, their use as catalysts and processes carried out in the presence of such transition metal complexes as catalysts.

According to the present invention, the radicals R1, R2, R5, R6, R7, R8 and R9 are each, independently of one another, hydrogen, an alkyl or alkylene group having from 1 to 8 carbon atoms or an alkoxy group having from 1 to 8 carbon atoms.

As alkyl or alkylene group having from 1 to 8 carbon atoms, preference is given to an alkyl group having from 1 to 8 carbon atoms, in particular from 1 to 4 carbon atoms, advantageously selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl.

As alkoxy group having from 1 to 8 carbon atoms, preference is given to an alkoxy group having from 1 to 4 carbon atoms, advantageously selected from the group consisting of methoxy, ethoxy, n-propoxy, i-propoxy, n-butoxy, s-butoxy, i-butoxy and t-butoxy, in particular methoxy.

In a preferred embodiment of a phosphonite I of the formula 1, it is advantageous for R1 and R2 each to be, independently of one another, an alkyl group having from 1 to 4 carbon atoms, preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl.

In a preferred embodiment of a phosphonite I of the formula 2, it is advantageous for R1 and R2 each to be, independently of one another, hydrogen, an alkyl group having from 1 to 4 carbon atoms, preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl, or an alkoxy group having from 1 to 4 carbon atoms, advantageously selected from the group consisting of methoxy, ethoxy, n-propoxy, i-propoxy, n-butoxy, s-butoxy, i-butoxy and t-butoxy, in particular methoxy. In a particularly preferred embodiment of a phosphonite I of the formula 2, R1 can be an alkyl group having from 1 to 4 carbon atoms, preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl, particularly preferably methyl, and R2 can be hydrogen or an alkoxy group having from 1 to 4 carbon atoms, advantageously selected from the group consisting of methoxy, ethoxy, n-propoxy, i-propoxy, n-butoxy, s-butoxy, i-butoxy and t-butoxy, in particular methoxy.

In a preferred embodiment of a phosphonite I of the formula 1 or the formula 2, it is advantageous for R5, R6, R7 and R8 each to be, independently of one another, hydrogen or an alkyl group having from 1 to 4 carbon atoms, preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl, in particular hydrogen or methyl.

According to the present invention, R3 is H or a methyl group.

According to the present invention, R4 is an i-propyl group or a t-butyl group.

Particularly preferred phosphonites I of the formula 1 are ones in which the radicals R1, R2, R3 and R9 are as shown in table 1 below.

TABLE 1

| No. | R1   | R2   | R3 | R9 |
|-----|------|------|----|----|
| 1   | Me   | Me   | H  | H  |
| 2   | Et   | Et   | H  | H  |
| 3   | n-Pr | n-Pr | H  | H  |
| 4   | t-Bu | t-Bu | H  | H  |
| 5   | Et   | Me   | H  | H  |
| 6   | n-Pr | Me   | H  | H  |
| 7   | t-Bu | Me   | H  | H  |
| 8   | Me   | Me   | H  | Me |
| 9   | Me   | Me   | H  | Me |
| 10  | t-Bu | Me   | Me | H  |

Particularly preferred phosphonites I of the formula 2 are ones in which the radicals R1 and R2 are as shown in table 2 below.

TABLE 2

| No. | R1 | R2  |
|-----|----|-----|
| 11  | Me | H   |
| 12  | Me | OMe |

Particularly preferred phosphonites I of the formulae 1 and 2 also include those in which the radicals R4, R5, R6, R7 and R8 are as shown in table 3 below.

TABLE 3

| No. | R4   | R5 | R6   | R7 | R8 |
|-----|------|----|------|----|----|
| 13  | i-Pr | H  | H    | H  | H  |
| 14  | i-Pr | H  | H    | Me | H  |
| 15  | i-Pr | H  | Me   | H  | H  |
| 16  | t-Bu | H  | H    | H  | H  |
| 17  | t-Bu | H  | H    | Me | H  |
| 18  | t-Bu | H  | Me   | H  | H  |
| 19  | t-Bu | H  | t-Bu | H  | H  |
| 20  | t-Bu | H  | H    | H  | Me |

In tables 1, 2 and 3, the abbreviations have the following meanings:
H: hydrogen
Me: methyl
Et: ethyl
n-Pr: n-propyl
t-Bu: t-butyl
OMe: methoxy According to the present invention, n is 1 or 2.

According to the present invention, X is F, Cl or $CF_3$, preferably F or $CF_3$.

In the case of n being 2, the two radicals X1 and X2 can be F, Cl or $CF_3$ independently of one another, i.e. F and F, F and Cl, F and $CF_3$, Cl and Cl, Cl and $CF_3$, $CF_3$ and $CF_3$, preferably F and F, $CF_3$ and $CF_3$.

In a preferred embodiment, when n is 1 and X is F, the substituent is present in the m position relative to the phosphorus atom bound to the phenyl ring.

In a further, preferred embodiment, when n is 1 and X is F, the substituent is present in the p position relative to the phosphorus atom bound to the phenyl ring.

In a further, preferred embodiment, when n is 1 and X is $CF_3$, the substituent is present in the p position relative to the phosphorus atom bound to the phenyl ring.

In a preferred embodiment, when n is 2 and X1 and X2 are each F, the substituents are present in the two m positions relative to the phosphorus atom bound to the phenyl ring.

In a further, preferred embodiment, when n is 2 and X is $CF_3$, the substituents are present in the two m positions relative to the phosphorus atom bound to the phenyl ring.

Phosphonite I can be prepared in a manner analogous to the preparative method described in WO 99/64155 for the phosphonite ligands of the formula I described there by firstly reacting an (Xn-phenyl)phosphorus(III) dihalide, preferably (Xn-phenyl)phosphorus(III) dichloride, with a phenol bearing the radicals R4, R5, R6, R7 and R8 to form an (Xn-phenyl)(R4, R5, R6, R7, R8-phenoxy)phosphorus (III) halide with elimination of hydrogen halide. If desired, this reaction product can be isolated and/or purified, e.g. by distillation, before further reaction by known methods.

The (Xn-phenyl)(R4, R5, R6, R7, R8-phenoxy)phosphorus(III) halide can then be reacted with a 2,2'-bisphenol bearing the radicals R1, R2, R3 and R9 in the case of formula 1 or a 2,2'-bisnaphthol bearing the radicals R1 and R2 in the case of the formula 2 to form a phosphonite I with elimination of hydrogen halide.

Both reactions can advantageously be carried out in the range from about 40 to about 200° C. Both reactions can be carried out in the presence of a base such as an aliphatic amine, for example, diethylamine, dipropylamine, dibutylamine, trimethylamine, triethylamine or tripropylamine, or pyridine, preferably triethylamine or pyridine. A purely thermal elimination of hydrogen halide is preferred in the first reaction step.

The preparation proceeds efficiently and economically from readily available starting materials.

The (Xn-phenyl)phosphorus(III) dihalides used as starting compounds and their preparation are known per se, for example from: H. Schindlbauer, Monatshefte Chemie, volume 96, 1965, pages 1936–1942. The process described there for preparing 4-fluorophenyldichlorophosphine can be employed analogously for preparing the other (Xn-phenyl) phosphorus(III) dihalides. The optimum parameters for preparing the respective (Xn-phenyl)phosphorus(III) dihalides can readily be determined by a few simple preliminary experiments.

The phosphonites I can be used as ligands in transition metal complexes.

Transition metals which can advantageously be used are the metals of transition groups I, II and VI to VIII of the Periodic Table, preferably transition group VIII of the Periodic Table, particularly preferably iron, cobalt and nickel, in particular nickel.

If nickel is used, it can be present in various oxidation states such as 0, +1, +2, +3. Preference is given to nickel(0) and nickel(+2), in particular nickel(0).

To prepare the transition metal complexes, a chemical compound of a transition metal or preferably a transition metal can be reacted with a phosphonite I, with the phosphonite I used being able to be either a single phosphonite I or a mixture of a plurality of phosphonites I.

Prior to the reaction, the transition metal can be obtained from suitable chemical compounds, e.g. salts such as chlorides, for example by reduction with base metals such as zinc.

If a transition metal compound is used for preparing the transition metal complexes, advantageous compounds are salts such as chlorides, bromides, acetylacetonates, sulfates, nitrates, for example nickel(2) chloride, or Ni(0) complexes such as bis(1,5-cyclooctadiene)Ni(0).

After the reaction of the transition metal compound or the transition metal with a phosphonite I, the oxidation state of the transition metal in the complex can be altered by means of suitable oxidizing or reducing agents, for example base metals such as zinc or hydrogen in chemically bound form, e.g. sodium borohydride, or in molecular form, or electrochemically.

In a particularly preferred embodiment, a complex of Ni(0) with organic monophosphine, monophosphinite, monophosphonite or monophosphite ligands can be reacted with a phosphonite I using a method based on that described in the German patent application 10136488.1.

In the transition metal complexes, the molar ratio of transition metal to phosphonite I can be in the range from 1 to 6, preferably from 2 to 5, in particular 2, 3 or 4.

The transition metal complexes can be free of ligands other than the phosphonites I.

The transition metal complexes may further comprise other ligands in addition to the phosphonites I, for example nitriles such as acetonitrile, adiponitrile, 3-pentenenitrile, 4-pentenenitrile, 2-methyl-3-butenenitrile, olefins such as butadiene or phosphorus compounds such as organic monophosphines, monophosphinites, monophosphonites or monophosphites.

The preparation of such transition metal complexes can be carried out by methods analogous to those described in the literature, for example in DE-A-2 237 703, U.S. Pat. No. 3,850,973, U.S. Pat. No. 3,766,237 or U.S. Pat. No. 3,903,120, for preparing transition metal complexes containing tri-o-tolyl phosphite, tri-m-tolyl phosphite or tri-p-tolyl phosphite ligands by replacing these phosphites partly or completely by the phosphonites I of the present invention.

The transition metal complexes of the present invention can be used as catalysts, in particular as homogeneous catalysts.

It has been found to be particularly advantageous to use the transition metal complexes of the present invention as catalysts in the addition of hydrocyanic acid onto olefinic double bonds, in particular double bonds which are conjugated with a further olefinic double bond, for example onto a double bonds of butadiene to give a mixture comprising 2-methyl-3-butenenitrile and 3-pentenenitrile. It is equally advantageous to use the transition metal complexes of the invention as catalysts in the addition of hydrocyanic acid onto olefinic double bond which are not conjugated with a further olefinic double bond, for example onto the double bond of 3-pentenenitrile or 4-pentenenitrile or mixtures thereof, preferably 3-pentenenitrile, to give adiponitrile, or onto 3-pentenoic esters or 4-pentenoic esters or mixtures thereof, preferably 3-pentenoic esters, to give 5-cyanovaleric esters.

It has likewise been found to be particularly advantageous to use the transition metal complexes of the present invention as catalysts in the isomerization of organic nitriles, in particular ones in which the nitrile group is not conjugated with an olefinic double bond, for example the isomerization of 2-methyl-3-butenenitrile to give 3-pentenenitrile. It is equally advantageous to use the transition metal complexes of the present invention as catalysts in the isomerization of organic nitriles in which the nitrile group is conjugated with an olefinic double bond.

Processes for the addition of hydrocyanic acid onto an olefinic double bond or for the isomerization of organic nitriles can be carried out in a manner analogous to that described, for example, in WO 99/13983 or WO 99/64155, by partly or completely replacing the phosphonites described there by the phosphonites I of the present invention.

The invention also provides a process for preparing mixtures of monoolefinic $C_5$-mononitriles having nonconjugated C=C and C=N bonds by hydrocyanation of a 1,3-butadiene-containing hydrocarbon mixture in the presence of at least one of the above described systems according to the present invention as catalyst.

The preparation of monoolefinic $C_5$-mononitriles by the process of the present invention is preferably carried out using, a hydrocarbon mixture having a 1,3-butadiene content of at least 10% by volume, preferably at least 25% by volume, in particular at least 40% by volume.

To prepare mixtures of monoolefinic $C_5$-mononitriles which comprise, for example, 3-pentenenitrile and 2-methyl-3-butenenitrile and are suitable as intermediates for further processing to produce adiponitrile, it is possible to use pure butadiene or 1,3-butadiene-containing hydrocarbon mixtures.

1,3-Butadiene-containing hydrocarbon mixtures are available on an industrial scale. Thus, for example, the processing of petroleum by steam cracking of naphtha produces a hydrocarbon mixture known as $C_4$ fraction which has a high total olefin content, with about 40% being 1,3-butadiene and the remainder being made up of monoolefins and multiply unsaturated hydrocarbons and also alkanes. These streams always contain small proportions of generally up to 5% of alkynes, 1,2-dienes and vinylacetylene.

Pure 1,3-butadiene can be isolated from industrially available hydrocarbon mixtures by, for example, extractive distillation.

$C_4$ fractions are, if desired, substantially freed of alkynes, e.g. propyne or butyne, of 1,2-dienes, e.g. propadiene, and of alkenynes, e.g. vinylacetylene. Otherwise, products in which a C=C double bond is conjugated with the C=N bond are sometimes obtained. It is known from "Applied Homogeneous Catalysis with Organometalic Compounds", vol. 1, VCH Weinheim, p. 479, that the conjugated 2-pentenenitrile formed in the isomerization of 2-methyl-3-butenenitrile and 3-pentenenitrile acts as a reaction inhibitor for the second addition of hydrogen cyanide to form adiponitrile. It has been found that the abovementioned conjugated nitrites obtained in the hydrocyanation of an unpretreated $C_4$ fraction also act as catalyst poisons for the first reaction step of the preparation of adipic acid, namely the monoaddition of hydrogen cyanide.

For this reason, it may be useful to free the hydrocarbon mixture partly or completely of components which form catalyst poisons in the catalytic hydrocyanation, in particular alkynes, 1,2-dienes and mixtures thereof. To remove these components, the $C_4$ fraction is subjected to a catalytic partial hydrogenation before the addition of hydrogen cyanide. This partial hydrogenation is carried out in the presence of a hydrogenation catalyst which is capable of selectively hydrogenating alkynes and 1,2-dienes in the presence of other dienes and monoolefins.

Suitable heterogeneous catalyst systems generally comprise a transition metal compound on an inert support. Suitable inorganic supports are the customary oxides, in particular silicon and aluminum oxides, aluminosilicates, zeolites, carbides, nitrides, etc., and mixtures thereof. Preference is given to using $Al_2O_3$, $SiO_2$ and mixtures thereof as supports. In particular, the heterogeneous catalysts used are those described in U.S. Pat. No. 4,587,369.; U.S. Pat. No. 4,704,492 and U.S. Pat. No. 4,493,906, which are hereby fully incorporated by reference. Further suitable catalyst systems based on Cu are marketed by Dow Chemical as KLP catalyst.

The addition reaction of hydrogen cyanide with 1,3-butadiene or a 1,3-butadiene-containing hydrocarbon mixture, e.g. a pretreated, partially hydrogenated $C_4$ fraction, can be carried out continuously, semicontinuously or batchwise.

In a useful variant of the process of the present invention, the addition reaction of the hydrogen cyanide is carried out continuously. Suitable reactors for a continuous reaction are known to those skilled in the art and are described, for example, in Ullmanns Enzyklopädie der technischen Chemie, vol. 1, 3rd edition, 1951, p. 743 ff. The continuous variant of the process of the present invention is preferably carried out using a cascade of stirred vessels or a tube reactor.

In a preferred variant of the process of the present invention, the addition reaction of hydrogen cyanide with 1,3-butadiene or a 1,3-butadiene-containing hydrocarbon mixture is carried out semicontinuously.

The semicontinuous process comprises:
a) charging a reactor with the hydrocarbon mixture, if desired part of the hydrogen cyanide and a hydrocyanation catalyst according to the present invention, if desired produced in situ, and, if desired, a solvent,
b) reacting the mixture at elevated temperature and superatmospheric pressure, with hydrogen cyanide being fed in at the rate at which it is consumed,
c) completing the conversion by a period of after-reaction and subsequently working up the mixture.

Suitable pressure-rated reactors are known to those skilled in the art and are described, for example, in Ullmanns Enzyklopädie der technischen Chemie, vol. 1, 3rd edition, 1951, p. 769 ff. In general, the process of the present invention is carried out using an autoclave which may, if desired, be provided with a stirrer and an internal lining. For the above steps, the following procedures/conditions are preferred:

Step a):

The pressure-rated reactor is charged with the partially hydrogenated $C_4$ fraction or butadiene, hydrogen cyanide, a hydrocyanation catalyst and, if desired, a solvent prior to commencement of the reaction. Suitable solvents are those mentioned above for the preparation of the catalysts of the present invention, preferably aromatic hydrocarbons such as toluene and xylene, or tetrahydrofuran.

Step b):

The mixture is generally reacted at elevated temperature and superatmospheric pressure. The reaction temperature is generally in a range from about 0 to 200° C., preferably from about 50 to 150° C. The pressure is generally in a range from about 1 to 200 bar, preferably from about 1 to 100 bar, in particular from 1 to 50 bar, particularly preferably from 1 to 20 bar. During the reaction, hydrogen cyanide is fed in at a rate corresponding to that at which it is consumed, with the pressure in the autoclave remaining essentially constant. The reaction time is from about 30 minutes to 5 hours.

Step c):

To complete the conversion, the reaction time can be followed by an after-reaction time of up to about 5 hours, preferably from about 1 hour to 3.5 hours, during which no more hydrogen cyanide is fed into the autoclave. During this time, the temperature is kept essentially constant at the reaction temperature set during the addition of hydrogen cyanide. Work-up is carried out by customary methods and comprises separating off the unreacted 1,3-butadiene and the unreacted hydrogen cyanide, e.g. by washing or extraction, and fractionally distilling the remaining reaction mixture to separate off the products of value and recover the still active catalyst.

In a further useful variant of the process of the present invention, the addition reaction of the hydrogen cyanide with the 1,3-butadiene-containing hydrocarbon mixture is carried out batchwise. Here, essentially the same reaction conditions as described for the semicontinuous process are maintained, but no additional hydrogen cyanide is fed in in step b). All of the hydrogen cyanide is included in the initial charge.

In general, the preparation of adiponitrile from a butadiene-containing mixture by addition of 2 molar equivalents of hydrogen cyanide can be divided into three steps:

1. Preparation of mixtures of $C_5$-monoolefins having a nitrile function.

2. Isomerization of the 2-methyl-3-butenenitrile present in these mixtures to form 3-pentenenitrile and isomerization of the 3-pentenenitrile formed in this way and the 3-pentenenitrile already present in the mixtures from step 1 to form various n-pentenenitriles. A very high proportion of 3-pentenenitrile or 4-pentenenitrile and a very small proportion of conjugated 2-pentenenitrile and 2-methyl-2-butenenitrile, which may act as catalyst poisons, should be formed.

3. Preparation of adiponitrile by addition of hydrogen cyanide onto the 4-pentenenitrile which has previously been formed in situ by isomerization of the 3-pentenenitrile formed in step 2. By-products formed are, for example, 2-methylglutaronitrile from the Markovnikov addition of hydrogen cyanide onto 4-pentenenitrile or the anti-Markovnikov addition of hydrogen cyanide onto 3-pentenenitrile and ethyl succinonitrile from the Markovnikov addition of hydrogen cyanide onto 3-pentenenitrile.

The novel catalysts based on phosphonite ligands can also be used advantageously for the structural isomerization and double bond isomerization in step 2 and/or the second addition of hydrogen cyanide in step 3.

Advantageously, the catalysts used according to the present invention not only display a high selectivity to the monoaddition products obtained in the hydrocyanation of 1,3-butadiene-containing hydrocarbon mixtures but they can also be admixed with an excess of hydrogen cyanide without appreciable deposition of inactive nickel(II) compounds, e.g. nickel(II) cyanide, occurring. In contrast to known hydrocyanation catalysts based on uncomplexed phosphine and phosphite ligands, the catalysts comprising a phosphonite I are thus suitable not only for continuous hydrocyanation processes in which an excess of hydrogen cyanide in the reaction mixture can generally be effectively avoided but also for semicontinuous processes and batch processes in which a large excess of hydrogen cyanide is generally present. The catalysts used according to the present invention and the hydrocyanation processes based on them generally display higher catalyst recycle rates and longer catalyst operating times than do known processes. Apart from the economic aspect, this is also advantageous for ecological reasons since the nickel cyanide formed by reaction of the active catalyst with hydrogen cyanide is highly toxic and has to be worked up or disposed of at high cost.

Apart from the hydrocyanation of 1,3-butadiene-containing hydrocarbon mixtures, the systems of the present invention are generally suitable for all customary hydrocyanation processes. Particular mention may be made of the hydrocyanation of unactivated olefins, e.g. styrene and 3-pentenenitrile.

The addition of hydrocyanic acid onto an olefinic double bond in the presence of a catalyst system according to the present invention, in particular the addition onto butadiene or onto 3-pentenenitrile, 4-pentenenitrile or a mixture of such pentenenitriles or the isomerization of organic nitriles in the presence of a catalyst system according to the present invention, in particular the isomerization of 2-methyl-3-butenenitrile to 3-pentenenitrile, can advantageously be carried out in the presence of one or more Lewis acids as promoters which influence the activity, selectivity or both of the catalyst system of the present invention. Possible promoters are inorganic and organic compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples which may be mentioned are $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O-iso-Pr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $ZrCl_2$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as are generally described, for example in U.S. Pat. No. 6,171,996 B1. Further suitable promoters are described in the patents U.S. Pat. No. 3,496,217, U.S. Pat. No. 3,496,218 and U.S. Pat. No. 4,774,353. These comprise metal salts such as $ZnCl_2$, $CoI_2$ and $SnCl_2$, and organometallic compounds such as $RAlCl_2$, $R_3SnO_3SCF_3$ and $R_3B$, where R is an alkyl group or aryl group. U.S. Pat. No. 4,874,884 describes the selection of synergistically effective combinations of promoters to increase the catalytic activity of the catalyst system. Preferred promoters include $CdCl_2$, $FeCl_2$, $ZnCl_2$, $B(C_6H_5)_3$ and $(C_6H_5)_3SnZ$, where Z is $CF_3SO_3$, $CH_3C_6H_4SO_3$ or $(C_6H_5)_3BCN$.

The molar ratio of promoter to nickel in the catalyst system can be in the range from 1:16 to 50:1.

A further advantageous embodiment of hydrocyanation and isomerization may be found in U.S. Pat. No. 5,981,772, whose contents are hereby incorporated by reference, with the proviso that a catalyst system according to the present invention or a mixture of such catalyst systems is used in place of the catalysts mentioned in the patent cited.

A further advantageous embodiment of hydrocyanation may be found in U.S. Pat. No. 6,127,567, whose contents are hereby incorporated by reference, with the proviso that a catalyst system according to the present invention or a mixture of such catalyst systems is used in place of the catalysts mentioned in the patent cited.

A further advantageous embodiment of hydrocyanation and isomerization may be found in U.S. Pat. No. 5,693,843, whose contents are hereby incorporated by reference, with the proviso that a catalyst system according to the present invention or a mixture of such catalyst systems is used in place of the catalysts mentioned in the patent cited.

A further advantageous embodiment of hydrocyanation may be found in U.S. Pat. No. 5,523,453, whose contents are hereby incorporated by reference, with the proviso that a catalyst system according to the present invention or a mixture of such catalyst systems is used in place of the catalyts mentioned in the patent cited.

The invention is illustrated by the following nonlimiting examples.

EXAMPLES

The yields were determined by gas chromatography (column: 30 m Stabil-Wachs, temperature program: 5 minutes isothermal at 50° C., then heating at a rate of 5° C./min to 240° C., gas chromatograph: Hewlett Packard HP 5890)

All examples were carried out under a protective argon atmosphere.

The abbreviation nickel(0)-(m/p-tolyl phosphite) is used for a mixture comprising 2.35% by weight of Ni(0), 19% by weight of 3-pentenenitrile and 78.65% by weight of m/p-tolyl phosphite having an m:p ratio of 2:1.

Chelating ligands used were:
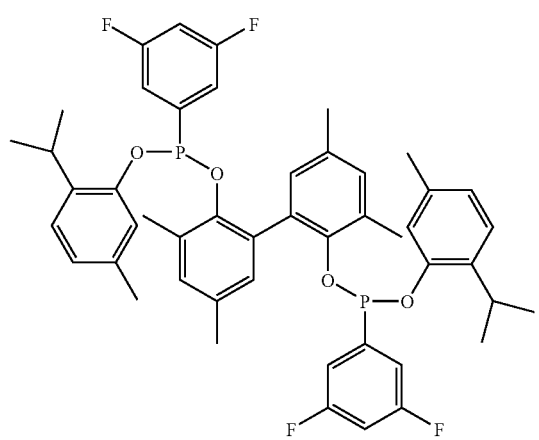
Ligand 1
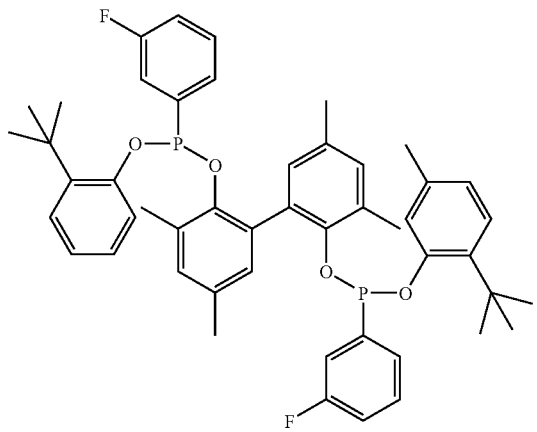
Ligand 4
Ligand 2
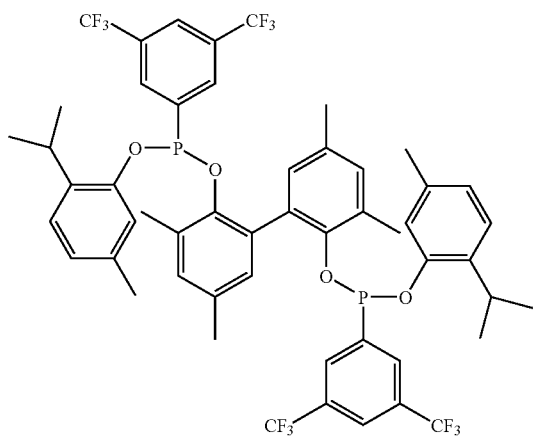
Ligand 5
Ligand 3
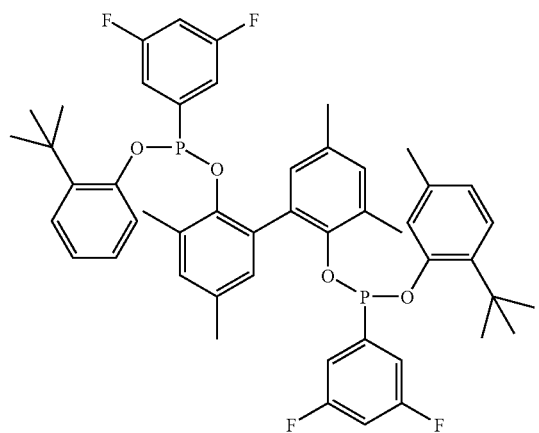
Ligand 6

Ni(COD)$_2$ is an abbreviation for bis(1,4-cyclooctadiene) Ni(0), 2M3BN for 2-methyl-3-butenenitrile, t2M2BN for trans-2-methyl-2-butenenitrile, c2M2BN for cis-2-methyl-2-butenenitrile, t2PN for trans-2-pentenenitrile, 4PN for 4-pentenenitrile, t3PN for trans-3-pentenenitrile, c3PN for cis-3-pentenenitrile, MGN for methylglutaronitrile, 3PN for the sum of t3PN and c3PN, BD for 1,3-butadiene, HCN for hydrocyanic acid, ADN for adiponitrile and THF for tetrahydrofuran.

Examples 1–2

Isomerization of 2-methyl-3-butenenitrile to 3-pentenenitrile

Example 1

(Comparison) (0.5 mmol of Ni(0))

1 equivalent of nickel(0)-(m-/p-tolyl phosphite) was admixed with 465 equivalents of 2M3BN and heated to 115° C. Samples were taken from the reaction mixture after 90 minutes and after 180 minutes and analyzed by gas chromatography (GC percent by area). The following results were obtained:

| Time | 2M3BN | t2M2BN | c2M2BN | t2PN | 4PN | t3PN, c3PN | 3PN/2 M3BN |
|---|---|---|---|---|---|---|---|
| 90 min | 84.5 | 1.3 | 0.3 | | | 13.0 | 0.15 |
| 180 min | 72.4 | 1.5 | 0.5 | | | 24.4 | 0.34 |

Example 2

(According to the Present Invention) (0.4 mmol of Ni(0))

1 equivalent of Ni(COD)$_2$ was admixed with 3 equivalents of ligand 1 and 465 equivalents of 2M3BN, stirred at 25° C. for 1 hour and then heated to 115° C. Samples were taken from the reaction mixture after 90 minutes and after 180 minutes and analyzed by gas chromatography (GC percent by area). The following results were obtained:

| Time | 2M3BN | t2M2BN | c2M2BN | t2PN | 4PN | t3PN | c3PN | 3PN/2M 3BN |
|---|---|---|---|---|---|---|---|---|
| 90 min | 35.84 | 0 | 0 | 0 | 0.14 | 56.62 | 3.04 | 1.66 |
| 180 min | 26.45 | 0 | 0 | 0 | 0.28 | 65.09 | 3.26 | 2.58 |

Examples 3–9

Hydrocyanation of 3-pentenenitrile to Form Adiponitrile

Example 3

(Comparison) (0.6 mmol of Ni(0))

1 equivalent of nickel(0)-(m-/p-tolyl phosphite) was admixed with 365 equivalents of 3PN, stirred at 25° C. for one hour and heated to 70° C. 1 equivalent of ZnCl$_2$ was added to this mixture and the mixture was stirred for a further 5 minutes. 94 equivalents of HCN/h*Ni in a stream of argon carrier gas were then introduced. Samples were taken from the reaction mixture after 30 minutes, 60 minutes and 150 minutes and analyzed by gas chromatography (GC percent by weight, internal standard: ethylbenzene). The following results were obtained:

| Time | MGN | ADN | ADN selectivity (%) |
|---|---|---|---|
| 30 min | 3.35 | 10.75 | 76.2 |
| 60 min | 6.87 | 26.39 | 79.3 |
| 150 min | 7.11 | 27.82 | 79.6 |

The amount of 2-PN after 60 minutes was 1.40%.

Example 4

(Comparison) (0.55 mmol of Ni(0))

1 equivalent of Ni(COD)$_2$ was admixed with 3 equivalents of ligand 2 and 365 equivalents of 3PN, stirred at 25° C. for one hour and heated to 70° C. 1 equivalent of ZnCl$_2$ was added to this mixture and the mixture was stirred for a further 5 minutes. 142 equivalents of HCN/h*Ni in a stream of argon carrier gas were then introduced. Samples were taken from the reaction mixture after 30 minutes and after 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 1.80 | 18.91 | 91.3 |
| 60 min | 2.51 | 32.57 | 92.9 |

The amount of 2PN formed was 2.80% after 60 minutes.

Example 5

(According to the Present Invention) (0.65 mmol of Ni(0))

1 equivalent of Ni(COD)$_2$ was admixed with 3 equivalents of ligand 1 land 365 equivalents of 3PN, stirred at 25° C. for one hour and heated to 70° C. 1 equivalent of ZnCl$_2$ was added to this mixture and the mixture was stirred for a further 5 minutes. 85 equivalents of HCN/h*Ni in a stream of argon carrier gas were then introduced. Samples were taken from the reaction mixture after 45 minutes and 60 minutes and analyzed by gas chromatography (GC percent by weight, internal standard: ethylbenzene). The following results were obtained:

| Time | MGN | ADN | ADN selectivity (%) |
|---|---|---|---|
| 45 min | 1.46 | 14.12 | 90.6 |
| 60 min | 1.92 | 21.60 | 91.8 |

The amount of 2PN formed was 0.31% after 60 minutes.

Example 6

(According to the Present Invention) (0.49 mmol of Ni(0))

1 equivalent of Ni(COD)$_2$ was admixed with 3 equivalents of ligand 3 and 365 equivalents of 3PN, stirred at 25° C. for one hour and heated to 70° C. 1 equivalent of ZnCl$_2$ was added to this mixture and the mixture was stirred for a further 5 minutes. 128 equivalents of HCN/h*Ni in a stream of argon carrier gas were then introduced. Samples were taken from the reaction mixture after 30 minutes and after 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 1.92 | 24.03 | 94.5 |
| 60 min | 1.93 | 38.05 | 95.2 |

The amount of 2PN formed was 0.89% after 60 minutes.

Example 7

(According to the Present Invention) (0.58 mmol of Ni(0))

1 equivalent of Ni(COD)$_2$ was admixed with 3 equivalents of ligand 4 and 365 equivalents of 3PN, stirred at 25° C. for one hour and heated to 70° C. 1 equivalent of ZnCl$_2$ was added to this mixture and the mixture was stirred for a further 5 minutes. 106 equivalents of HCN/h*Ni in a stream of argon carrier gas were then introduced. Samples were taken from the reaction mixture after 30 minutes and 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 1.32 | 16.61 | 92.6 |
| 60 min | 2.20 | 36.17 | 94.3 |

The amount of 2PN formed was 1.12% after 60 minutes.

Example 8

(According to the Present Invention) (0.60 mmol of Ni(0))

1 equivalent of Ni(COD)$_2$ was admixed with 3 equivalents of ligand 6 and 365 equivalents of 3PN, stirred at 25° C. for one hour and heated to 70° C. 1 equivalent of ZnCl$_2$ was added to this mixture and the mixture was stirred for a further 5 minutes. 123 equivalents of HCN/h*Ni in a stream of argon carrier gas were then introduced. Samples were taken from the reaction mixture after 30 minutes and 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 2.24 | 24.17 | 91.5 |
| 60 min | 3.57 | 46.91 | 92.9 |

The amount of 2PN formed was 1.20% after 60 minutes.

Example 9

(According to the Present Invention) (0.65 mmol of Ni(0))

1 equivalent of nickel(0)-(m-/p-tolyl phosphite) was admixed with 3 equivalents of ligand 6 and 365 equivalents of 3PN, stirred at 25° C. for one hour and heated to 70° C. 1 equivalent of ZnCl$_2$ was added to this mixture and the mixture was stirred for a further 5 minutes. 127 equivalents of HCN/h*Ni in a stream of argon carrier gas were then introduced. Samples were taken from the reaction mixture after 30 minutes and 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 1.66 | 20.93 | 92.6 |
| 60 min | 2.74 | 32.36 | 92.2 |

The amount of 2PN formed was 1.02% after 60 minutes.

Examples 10–14

Hydrocyanation of Butadiene to Form 3-pentenenitrile

Example 10

(Comparison) (1 mmol of Ni(0))

1 equivalent of nickel(0)-(m-/p-tolyl phosphite) was admixed with 500 equivalents of BD and 420 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene. The following results were obtained:

| Time | Internal temperature |
|---|---|
| 30 min | 80.3 |
| 50 min | 80.5 |
| 60 min | 80.4 |
| 180 min | 80.3 |

Virtually no temperature increase occurs. This means that the catalyst is not very active.

The conversion of HCN into 2M3BN/3PN was 9.8%. The ratio of 2M3BN/3PN was 1/3.4.

Example 11

(Comparison) (1 mmol of Ni(0))

1 equivalent of Ni(COD)$_2$ was stirred with 3 equivalents of ligand 2 in THF for 20 minutes. This solution was admixed with 557 equivalents of BD and 433 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time | Internal temperature |
|---|---|
| 15 min | 82.2 |
| 30 min | 82.1 |
| 120 min | 81.1 |

Virtually no temperature increase occurs. This means that the catalyst is not very active.

The conversion of HCN into 2M3BN/3PN was 97.5%. The ratio of 2M3BN/3PN was 1.5/1.

Example 12

(Comparison) (1 mmol of Ni(0))

1 equivalent of nickel(0)-(m-/p-tolyl phosphite) was stirred with 1.2 equivalents of ligand 2 in THF for 12 hours. This solution was admixed with 480 equivalents of BD and 400 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time | Internal temperature |
|---|---|
| 30 min | 83.6 |
| 60 min | 84.5 |

-continued

| Time | Internal temperature |
|---|---|
| 120 min | 84.4 |
| 180 min | 80.5 |

The conversion of HCN into 2M3BN/3PN was >99%. The ratio of 2M3BN/3PN was 1.35/1.

Example 13

(According to the Present Invention) (1 mmol of Ni(0))

1 equivalent of Ni(COD)$_2$ was stirred with 3 equivalents of ligand 5 in THF for 20 minutes. This solution was admixed with 481 equivalents of BD and 400 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time | Internal temperature |
|---|---|
| 3 min | 90 |
| 4 min | 147 |
| 10 min | 98 |
| 120 min | 80 |

The conversion of HCN into 2M3BN/3PN was above 99%. The ratio of 2M3BN/3PN was 1/1.16.

Example 14

(According to the Present Invention) (1 mmol of Ni(0))

1 equivalent of nickel(0)-(m-/p-tolyl phosphite) was stirred with 1.2 equivalents of ligand 5 in THF for 12 hours. This solution was admixed with 448 equivalents of BD and 400 equivalents of HCN in THF, placed in a glass autoclave at 25° C. and heated to 80° C.

| Time | Internal temperature |
|---|---|
| 5 min | 87 |
| 10 min | 139 |
| 15 min | 107 |
| 120 min | 80 |

The conversion of HCN into 2M3BN/3PN was above 99%. The ratio of 2M3BN/3PN was 1.26/1.

We claim:
1. A phosphonite I of the formula 1 or 2

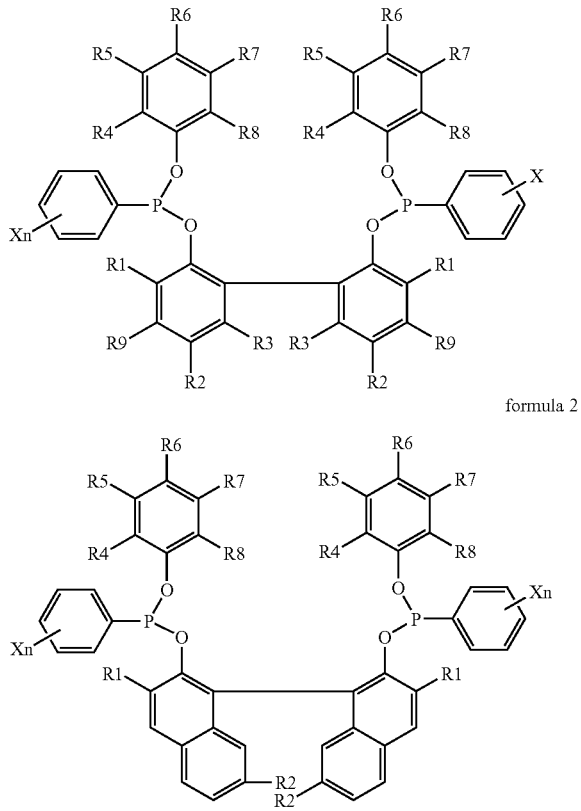

formula 1 formula 2 where
R1, R2, R5, R6, R7, R8, R9 are each, independently of one another, hydrogen, an alkyl or alkylene group having from 1 to 8 carbon atoms or an alkoxy group having from 1 to 8 carbon atoms,
R3 is H or methyl,
R4 is i-propyl or t-butyl,
X is F, Cl or $CF_3$ n is 1 or 2.

2. A phosphonite I as claimed in claim 1 in which R1, R2 are selected independently from the group consisting of methyl, ethyl, n-propyl, i-propyl and t-butyl.

3. A transition metal complex comprising a phosphonite I as claimed in claim 1 as ligand.

4. A transition metal complex as claimed in claim 3, wherein the transition, metal used is nickel.

5. A process for preparing transition metal complexes as claimed in claim 3 or 4 which comprises reacting an elemental transition metal or a chemical compound containing a transition metal with a phosphonite of the formula I.

6. A catalyst comprising a transition metal complex as claimed in claim 3.

7. A process comprising adding hydrocyanic acid onto an olefinic double bond in the presence of a catalyst comprising the transition metal complex as claimed in claim 4.

8. A process as claimed in claim 7, wherein hydrocyanic acid is added onto butadiene to give a compound selected from the group consisting of 2-methyl-3-butenenitrile and 3-pentenenitrile.

9. A process comprising isomerization of organic nitriles in the presence of a catalyst comprising the transition metal complex as claimed in claim 4.

10. A process as claimed in claim 9, wherein 2-methyl-3-butenenitrile is isomeric to 3-pentenenitrile.

11. A process as claimed in claim 7, wherein hydrocyanic acid is added onto 3-pentenenitrile, 4-pentenenitrile or a mixture thereof to give adiponitrile.

* * * * *